United States Patent
Hynynen et al.

(10) Patent No.: US 10,258,314 B2
(45) Date of Patent: Apr. 16, 2019

(54) SYSTEMS AND METHODS FOR SUPER-RESOLUTION ULTRASOUND IMAGING

(71) Applicants: Kullervo Hynynen, Toronto (CA); Meaghan O'Reilly, Toronto (CA); Foroohar Foroozan, Richmond Hill (CA)

(72) Inventors: Kullervo Hynynen, Toronto (CA); Meaghan O'Reilly, Toronto (CA); Foroohar Foroozan, Richmond Hill (CA)

(73) Assignee: SUNNYBROOK RESEARCH INSTITUTE, Toronto (CA)

( * ) Notice: Subject to any disclaimer, the term of this patent is extended or adjusted under 35 U.S.C. 154(b) by 430 days.

(21) Appl. No.: 14/888,523

(22) PCT Filed: May 2, 2014

(86) PCT No.: PCT/US2014/036567
§ 371 (c)(1),
(2) Date: Nov. 2, 2015

(87) PCT Pub. No.: WO2014/179681
PCT Pub. Date: Nov. 6, 2014

(65) Prior Publication Data
US 2016/0106395 A1     Apr. 21, 2016

Related U.S. Application Data

(60) Provisional application No. 61/819,346, filed on May 3, 2013.

(51) Int. Cl.
*A61B 8/08* (2006.01)
*A61B 8/00* (2006.01)
(Continued)

(52) U.S. Cl.
CPC .......... *A61B 8/5238* (2013.01); *A61B 8/0891* (2013.01); *A61B 8/4494* (2013.01);
(Continued)

(58) Field of Classification Search
CPC ... A61B 8/0808; A61B 8/0891; A61B 8/4494; A61B 8/481; A61B 8/5207
See application file for complete search history.

(56) References Cited

U.S. PATENT DOCUMENTS 5,052,394 A    10/1991   Carpenter et al.
5,230,340 A     7/1993   Rhyne
(Continued)

OTHER PUBLICATIONS

International Search Report and Written Opinion dated Oct. 7, 2014 in connection with PCT/US2014/036567.

*Primary Examiner* — Baisakhi Roy
(74) *Attorney, Agent, or Firm* — Quarles & Brady LLP

(57) ABSTRACT

Systems and methods for ultrasound imaging capable of achieving spatial resolutions that can resolve objects smaller than 300 μm are described. Ultrasound is transmitted to and steered over a volume-of-interest that contains a microbubble contrast agent to individually excite microbubbles. Signal data is acquired in response to the transmitted ultrasound, and a plurality of images are reconstructed by beamforming the acquired signal data. The spatial resolution of the beamformed images can be further increased using techniques that determine the position of the microbubble within each image to a greater level of accuracy than the point spread function ("PSF") of the ultrasound system. The images can also be combined to produce a single high resolution image of the volume-of-interest using, for instance, a maximum pixel projection technique.

11 Claims, 2 Drawing Sheets

(51) Int. Cl.
*G01S 7/52* (2006.01)
*G01S 15/89* (2006.01)

(52) U.S. Cl.
CPC ............ *A61B 8/481* (2013.01); *A61B 8/5207* (2013.01); *A61B 8/5246* (2013.01); *A61B 8/54* (2013.01); *G01S 7/52039* (2013.01); *G01S 7/52047* (2013.01); *G01S 7/52049* (2013.01); *A61B 8/0808* (2013.01); *G01S 15/8922* (2013.01); *G01S 15/8929* (2013.01)

(56) References Cited

U.S. PATENT DOCUMENTS

| | | | |
|---|---|---|---|
| 5,456,257 A | 10/1995 | Johnson et al. | |
| 5,934,288 A | 8/1999 | Avila et al. | |
| 6,126,603 A * | 10/2000 | Hatfield | A61B 8/06 600/443 |
| 6,186,949 B1 * | 2/2001 | Hatfield | G01S 7/52039 128/916 |
| 7,330,565 B1 * | 2/2008 | Der | G06K 9/3241 340/933 |
| 7,978,346 B1 | 7/2011 | Riza | |
| 2003/0092987 A1 * | 5/2003 | Hynynen | A61B 8/0858 600/437 |
| 2006/0052699 A1 * | 3/2006 | Angelsen | A61B 8/14 600/437 |
| 2007/0016051 A1 * | 1/2007 | Trucco | A61B 8/481 600/458 |
| 2007/0123110 A1 * | 5/2007 | Schwartz | A61B 8/14 439/638 |
| 2008/0161696 A1 * | 7/2008 | Schmitt | A61B 5/0066 600/467 |
| 2009/0036772 A1 | 2/2009 | Lu | |
| 2012/0170714 A1 | 12/2012 | Owen | |
| 2013/0011078 A1 | 1/2013 | Phan et al. | |
| 2013/0195341 A1 * | 8/2013 | Liu | G06T 11/005 382/131 |
| 2015/0148659 A1 * | 5/2015 | Vahala | A61N 7/022 600/411 |

* cited by examiner

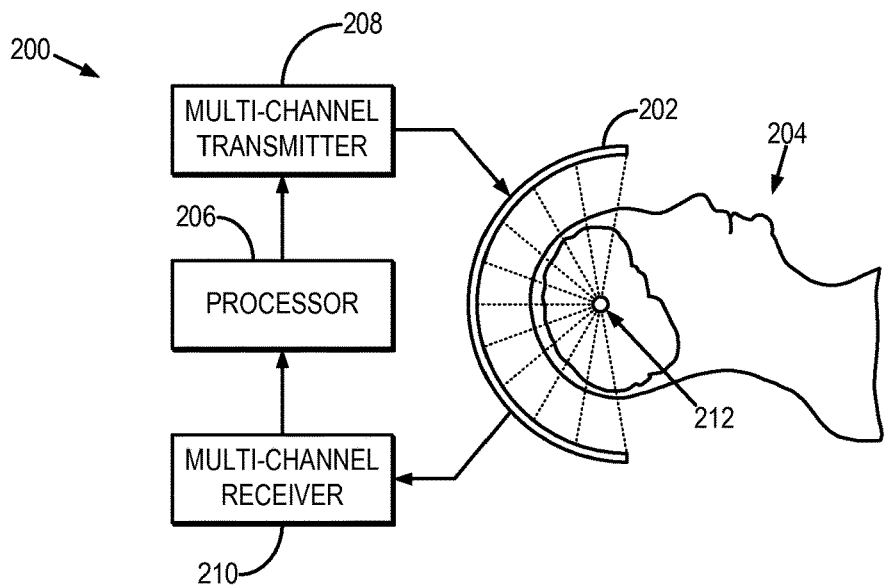
FIG. 2
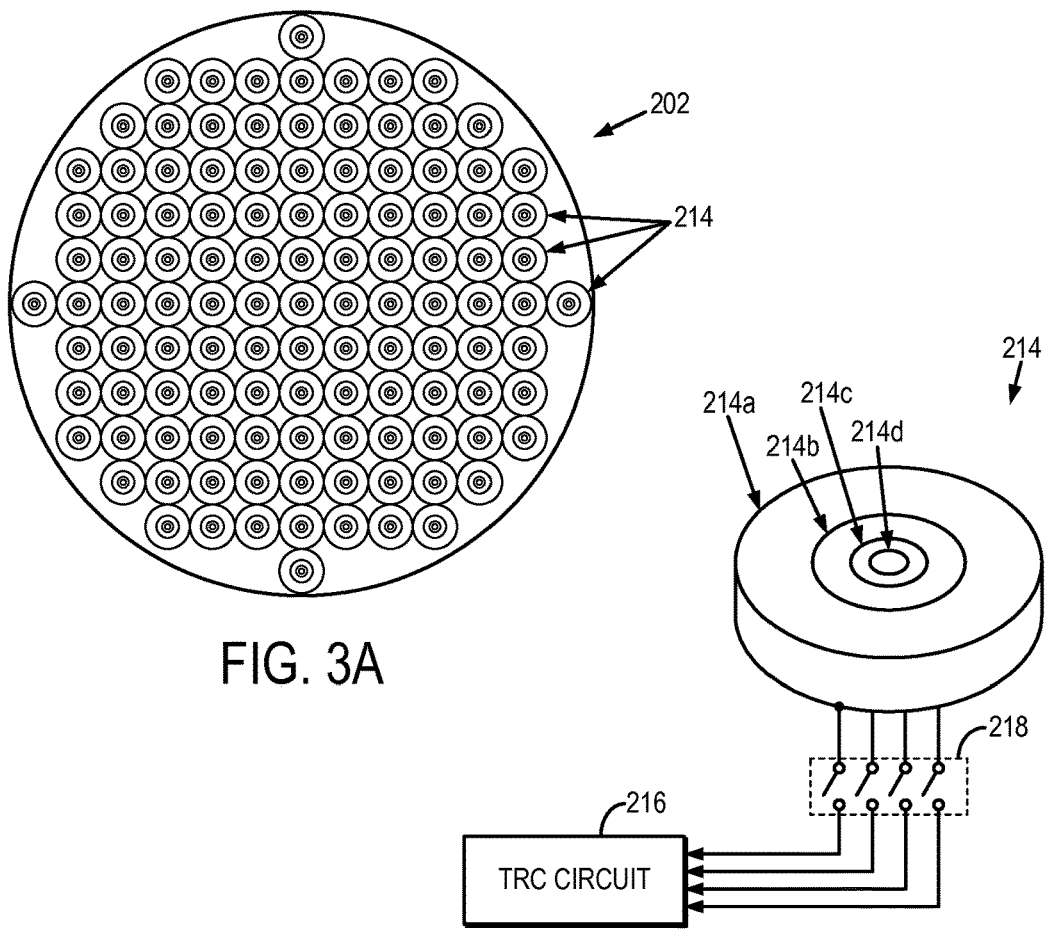
FIG. 3A
FIG. 3B

SYSTEMS AND METHODS FOR SUPER-RESOLUTION ULTRASOUND IMAGING

CROSS-REFERENCE TO RELATED APPLICATIONS

This application represents the national stage entry of PCT International Application No. PCT/US2014/036567, filed on May 2, 2014, which claims the benefit of U.S. Provisional Patent Application Ser. No. 61/819,346, filed on May 3, 2013, the disclosures of which are hereby incorporated by reference in their entirety for all purposes.

STATEMENT REGARDING FEDERALLY SPONSORED RESEARCH

This invention was made with government support under EB003268 and EB009032 awarded by the National Institutes of Health. The government has certain rights in the invention.

BACKGROUND OF THE INVENTION

The field of the invention is systems and methods for ultrasound imaging. More particularly, the invention relates to systems and methods for high resolution ultrasound imaging capable of sub-millimeter resolutions.

There is a need for vascular imaging in the brain that is not met with available clinical imaging modalities. Using computed tomography ("CT"), vessels with a diameter below 400 µm are not consistently detected.

With magnetic resonance imaging ("MRI") at a field strength of 1.5 T, the limit for vessel detection is approximately 300 µm. With increasing field strength, vessels with smaller diameters can be detected, leading to a greater number of vessels detected at higher field strengths such as 3 T or 7 T. At a field strength of 8 T, vessels estimated to be smaller than 100 µm have been imaged in the human brain. Despite the advances in spatial resolution, MRI remains a costly imaging modality with limited availability, and ultra-high field MRI scanners (e.g., those with field strengths greater than 7 T) that can detect smaller vessels are not found in routine clinical practice. Even at these high field strengths, the ability of MRI to image the smaller vessels that play a key role in many diseases and functions of the brain is limited.

Ultrasound is an imaging modality that does not use ionizing radiation, and that has additional advantages in both its relative low cost and portability. The use of ultrasound in the brain, however, has been severely limited by the attenuating and aberrating effects of the skull bone, which increase with increasing ultrasound frequency. Ultrasound imaging through the skull is thus typically performed at lower frequencies (e.g., 2-4 MHz) through thin acoustic windows in the skull. Because the spatial resolution achievable with ultrasound operating in traditional pulse-echo mode is dependent on frequency, imaging vessels in the brain with this approach sacrifices resolution, which has limited the use of ultrasound to the imaging of major vessels.

SUMMARY OF THE INVENTION

The present invention overcomes the aforementioned drawbacks by providing a method for ultrasound imaging, in which high resolution images are generated. For instance, the high resolution images are capable of resolving objects smaller than 300 µm. Ultrasound is transmitted to a focal region in a volume-of-interest that contains at least one microbubble, and this transmit focus can be steered over the volume-of-interest. Signal data is acquired in response to the transmitted ultrasound, and a plurality of initial images are reconstructed by beamforming the acquired signal data. A position of the at least one microbubble is estimated in each of the initial images, and phase and amplitude correction factors are computed using these position estimates and the initial images. A plurality of target images are then reconstructed by beamforming the acquired signal data using the computed phase and amplitude correction factors. An image having a higher spatial resolution than the target images is then produced by, for example, estimating the position of each bubble in each of the target images and fitting a function to the data based on the position estimates and uncertainty.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 2 is a block diagram of an example of an ultrasound system;

FIG. 3A is an example of a hemispherical transducer array that may form a part of the ultrasound system of FIG. 2; and FIG. 3B is an example of a transmit-receive transducer element that may form a part of the transducer array of FIG. 3A.

DETAILED DESCRIPTION OF THE INVENTION

Figure 1:
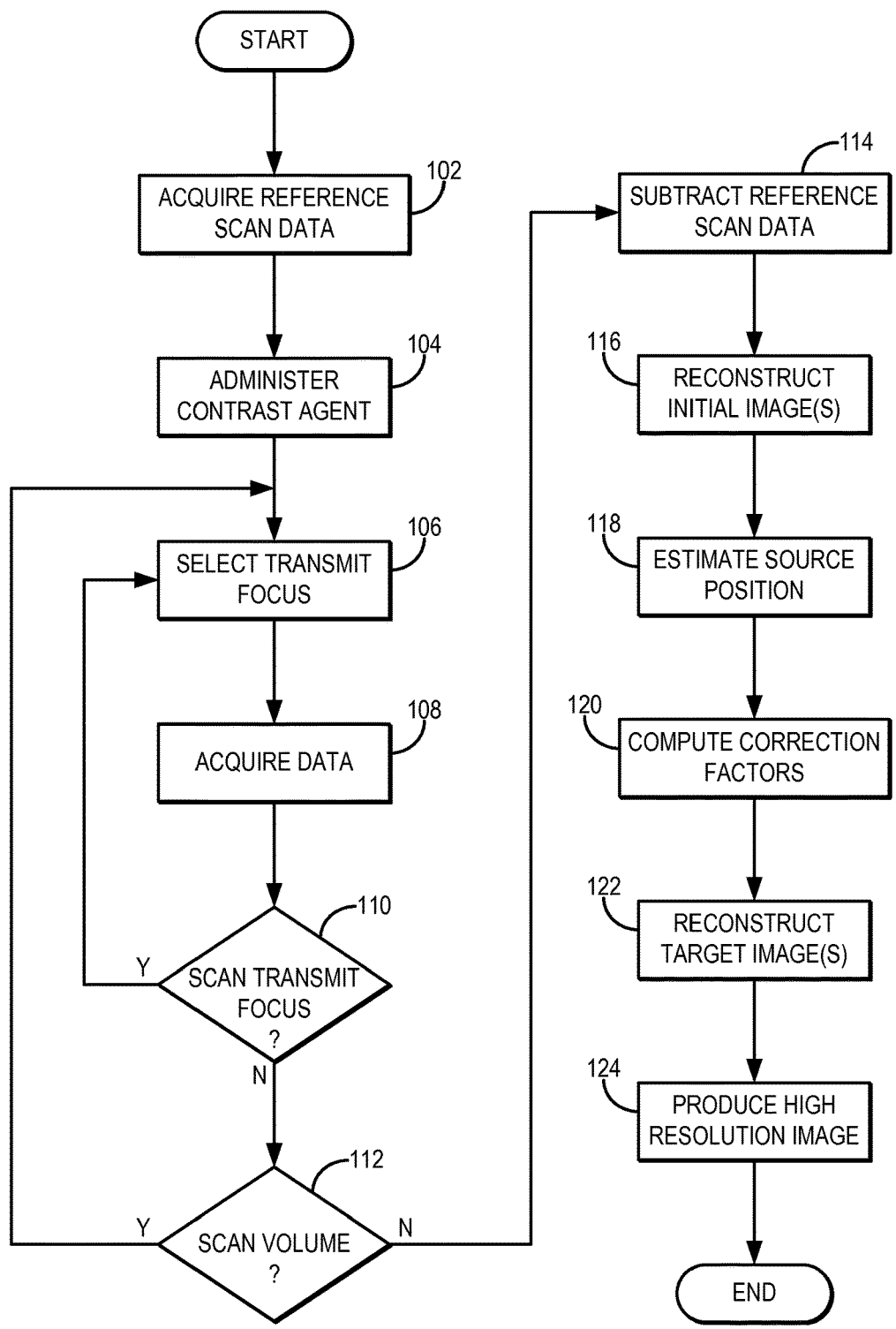
FIG. 1 is a flowchart setting forth the steps of an example of a method for reconstructing a high resolution image using an ultrasound system.

Described here are systems and methods for super-resolution ultrasound imaging. Instead of traditional pulse-echo imaging, a passive beamforming technique is used. With the passive beamforming technique, both the phase and amplitude information of the received signals are considered and axial resolution no longer depends on pulse length, but on frequency and array aperture. Additionally, the intensity of the scatter response can be integrated over time to significantly improve the signal-to-noise ratio ("SNR"). To overcome the skull attenuation, a low frequency transmit array can be used. To increase spatial resolution, a full hemispherical sparse receiver array can be used. Large aperture transmit arrays have been used for transcranial ultrasound therapy research, but have not been used for brain imaging to date.

Micrometer sized gas bubbles are exceptional scatters of ultrasound and have been used as intravascular contrast agents for over two decades. Using a hemispherical array, such as the one described below, and using passive beamforming, the imaging resolution for a given frequency can be optimized and sufficient SNR to image single bubbles through a human skullcap can be achieved. Here, single microbubbles are transcranially excited and three-dimensional passive maps of the bubbles are generated using a bubble-based phase correction technique. The result is a high resolution, transcranial, diffraction limited image of the vessels in which the microbubbles are located.

Additional techniques can be used to further improve the imaging resolution. For instance, the position of a distinct source within an image can be determined to a much greater level of accuracy than the point spread function ("PSF"). This has been applied to optics, combined with techniques to isolate distinct sources within the initial normal resolution images, to allow imaging well beyond the diffraction limit. These ideas, and the fact that microbubbles move with blood flow, are utilized to provide a method to enhance the three dimensional resolution of transcranial imaging beyond the diffraction limit.

Referring now to FIG. 1, a flowchart setting forth the steps of an example of a method for producing super high resolution images with an ultrasound system is illustrated. The method begins with the acquisition of reference scan data, as indicated at step 102. After the reference scan data has been acquired, a microbubble contrast agent is administered to the subject, as indicated at step 104. By way of example, the microbubble contrast agent is provided with a lower concentration that is conventionally used in other imaging applications. For instance, the contrast agent can be provided with a concentration of approximately 1600 microbubbles per milliliter. This low concentration of microbubbles ensures that a single microbubble can be selectively excited. An example of a contrast agent suitable for the purposes described here is the Definity™ microbubble contrast agent (Lantheus Medical Imaging, North Billerica, Mass., USA), which includes microbubbles with a mean diameter of 1-3 µm.

While the microbubble contrast agent is present in the volume-of-interest to be imaged, such as a blood vessel in a subject, data is obtained by exciting microbubbles, such as one microbubble at a time, and recording signals received in response to that excitation. Thus, as indicated at step 106, the method proceeds by selecting an ultrasound transmit focal point. Signals are then acquired by exciting the microbubble located in the focal spot and recording the signals received in response to that excitation, as indicated at step 108. This process is repeated for a plurality of different focal points in the volume-of-interest, as indicated by decision block 110. For example, the transmit focus can be electronically steered through the volume-of-interest through a plurality of different focal points in incremental steps, such as steps of 2 mm, in which the received waveforms are then recorded at each of these locations.

By scanning the transmit focus through the volume-of-interest, it is possible to excite different bubbles in different portions of the volume to create an image of the larger structure (e.g., the blood vessel or vessels) present in the volume-of-interest. Because the contrast agent is very dilute, after a single scan through the volume it is possible that only a partial image of the volume will have been obtained. However, because the bubbles move with the blood flowing through the volume-of-interest, multiple scans of the same volume can be performed to produce a complete image of the volume-of-interest, as indicated at decision block 112.

After the desired amount of data has been obtained, images of the volume-of-interest are reconstructed as follows. First, the reference scan data that was obtained earlier is subtracted from the data acquired in the presence of the contrast agent, as indicated at step 114. In doing this subtraction, strong reflections from the skull bone are suppressed. For instance, the reference scan data can be subtracted line-by-line from the data acquired after microbubbles have been introduced to the volume-of-interest in order to suppress reflections from the skull.

Next, initial uncorrected images are reconstructed, as indicated at step 116. These images are reconstructed using geometric delays to beamform the images over a reconstruction grid, with or without the inclusion of additional delay and amplitude compensation terms to account for the effects of the skull. The intensity value assigned to a voxel in the reconstructed image can be mathematically expressed as the summation of the magnitude of the power spectrum over a frequency band having a bandwidth of M discrete points centered about a center frequency having discrete indices, $m_c$:

$$I(r) = \sum_{m=m_c-\frac{M}{2}}^{m_c+\frac{M}{2}} \left| \sum_i Q_i(r; f_m) \right|^2; \quad (1)$$

where $I(r)$ is the image intensity at a point, $r=(x,y,z)$, in the reconstruction grid, and $Q_i(r;f_m)$ is the value at the $m^{th}$ frequency band of the discrete Fourier transform of the time-delayed waveform, $q_i(r;t)$, for the $i^{th}$ receiver element and point, r, over a window of N points:

$$Q_i(r; f_m) = \sum_{n=n_0}^{n_0+(N-1)} q_i(r; t_n) \cdot e^{-j2\pi mn/N}; \quad (2)$$

The time-delayed waveform, $q_i(r;t_n)$, can be expressed as:

$$q_i(r; t_n) = a_i \cdot p_i\left(t_n - \frac{\|r_i - r\|}{c} - s_i\right); \quad (3)$$

where $a_i$ is an amplitude correction term, $p_i(t)$ is the pressure value recorded by the $i^{th}$ receiver element at time, t; $r_i$ is a vector of the coordinates of the $i^{th}$ receiver element; c is the speed of sound in the medium; $s_i$ is a delay term to compensate for the effect of the skull on the waveform received by the $i^{th}$ receive element; and $\|\ldots\|$ represents the Euclidean norm. For a given skull geometry and orientation, the skull delay parameters, $s_i$, will be a function of the source location and receiver element location, but over a small reconstruction grid it is acceptable to use a single correction per receive element for all the grid points since the sound is incident on the same skull regions. For the same reason, and since variations due to spherical spreading will be small over a small volume, the amplitude correction terms, $a_i$, can also be approximated by a single correction per element over a small reconstruction grid. The amplitude and phase correction terms, $a_i$ and $s_i$, may also be functions of frequency.

By way of example, the initial images can be reconstructed by summing the power spectrum of a small time-window (e.g., 40 µs) at the point of the expected bubble response over a narrow range of frequencies (e.g., 100 kHz) about the center frequency of the receivers. For excitations resulting in a strong microbubble response, an initial distorted image and an initial estimate of the source location can be achieved. Thus, using the initial images, the location of the source (e.g., the excited microbubble) can be estimated, as indicated at step 118. By way of example, the source location can be estimated by fitting a three-dimensional Gaussian to the image. In this example, the three-dimensional Gaussian is selected because it is an approximation of the expected shape of the main lobe of the hemispherical transducer array described above. The Gaussian can be given a fixed standard deviation in each of the three dimensions based on an experimentally determined point spread function ("PSF") of the transducer array near the geometric focus. However, translation and rotation can be allowed in the fit.

The skull delay parameters, $s_i$, and amplitude correction terms, $a_i$, are then computed from the acoustic emissions from a single microbubble, as indicated at step 120. As noted above, the source position is estimated from the initial images reconstructed as described above. The geometric delays associated with this source location are determined. A matched-filter is then used to determine the total time delays between the receive elements. By way of example, the individual channels can be digitally filtered with a narrowband fourth-order Butterworth band-pass filter (400-800 kHz) prior to applying the matched filter. The skull delays are then determined as the difference between the total time delays with respect to one channel, and the geometric delays with respect to that reference channel. The amplitude correction terms can be determined as the reciprocal of the maximum value in each channel over a 15 µs time window over the bubble response, as identified by the matched filter. As noted above, the skull corrections calculated from a single bubble may be applied to correct all sources within a small imaging volume since the regions of the skull penetrated by the sound do not substantially change, and spherical spreading effects will be small over a small volume.

Using the computed correction factors, target phase and amplitude corrected images are reconstructed using the beamforming described above, as indicated at step 122. As an example, the images can be produced using a time window of 40 µs and a frequency interval of 100 kHz centered about 600 kHz.

A single, high resolution image of the volume-of-interest is then produced from the target images, as indicated at step 124. Target image frames that did not contain one clear source are preferably discarded and not used to produce the high resolution image. By way of example, target image frames can be selected for exclusion if they contain a local maximum with intensity greater than or equal to fifty percent of the global maximum in the frame. The single, high resolution image of the volume is then produced by normalizing the remaining target image frames to themselves and then combining the images using a maximum pixel projection technique. The response from the microbubbles is expected to vary, and strong responses would bias the high resolution image; hence, the frames without a clear main lobe are removed and the remaining frames are normalized to their respective maxima before taking the maximum pixel projection.

By way of example, to obtain the high resolution images, a three-dimensional Gaussian was fit to the target images in the same manner as described above. This fit is performed for each of the target image frames containing a clear source. High resolution frames can be plotted as a Gaussian centered at the estimated source location and having standard deviations in the three dimensions equal to the uncertainties on the position estimate. The complete high resolution image may be obtained by combining the normalized frames and taking the maximum pixel projection. As an example, a final high resolution image can be composed from hundreds of individually excited bubbles, such as four-hundred or more individually excited bubbles. It is noted that target image frames can also be excluded from this combination if the uncertainties on their positional estimates are deemed to be outliers. As an example, values greater than 1.5 times the interquartile range beyond the third quartile can be considered outliers.

Another method can utilize the time-varying nature of the bubble emissions to generate the high resolution images. For example, multiple quasi-static frames of the same bubble might be used to form the super-resolution image.

By way of example, the method of the present invention can be carried out using an ultrasound system such as the one illustrated in FIG. 2. The ultrasound system 200 generally includes a transducer array 202 that is capable of delivering ultrasound to a subject 204 and receiving responsive signals therefrom. For brain imaging application, the transducer array 202 is preferably configured to surround an extent of the subject's head. For example, the transducer array 202 may be an approximately hemispherical array of transducer elements.

The ultrasound system 200 generally includes a processor 206 that is in communication with a multi-channel transmitter 208 and a multi-channel receiver 210. The multi-channel transmitter 208 receives driving signals from the processor 206 and, in turn, directs the transducer elements of the transducer array 202 to generate ultrasound energy. The multi-channel receiver 210 receives acoustic signals during and/or after sonications and relays these signals to the processor 206 for processing in accordance with embodiments of the present invention. The processor 206 may also be configured to adjust the driving signals in response to the acoustic signals received by the multi-channel receiver 210. For example, the phase and/or amplitude of the driving signals may be adjusted so that ultrasound energy is more efficiently transmitted through the skull of the subject 204 and into the target volume-of-interest 212. Furthermore, the acoustic signals may also be analyzed to determine whether and how the extent of the focal region should be adjusted.

By way of example, the transducer array 202 may be an approximately hemispherical phased array with multiple transmit-receive ultrasound elements sparsely distributed in such a manner that the variation in the distance between elements is maximized. The diameter of the array 202 may be, for example, 30 centimeters. The array 202 may contain, for example, 128, 256, or more elements that are mounted on a hemispherical surface. As one example, these elements may be concentric cylindrical elements. Alternatively, the elements can be non-concentric cylindrical elements, or other shaped elements that may or may not be concentric. As another alternative, each transducer element can operate independently as transmit or receive elements that are individually distributed rather than combined in a single location.

In one example configuration illustrated in FIGS. 3A and 3B, the transmit-receive elements 214 in the transducer array 202 are composed of concentric cylindrical elements, 214a, 214b, 214c, 214d, that connect to a transmit/receive circuit ("TRC") 216 via a switch 218. The outermost element 214a can be, for example, a 250 kHz piezoelectric cylindrical annulus. As an example, the outermost element 214a can have a diameter of 2.54 mm. The next concentric element 214b is a cylindrical annulus with dimensions approximately half of the dimensions of the outermost element 214a. This sizing results in the maximum transmit signal of element 214b to be roughly double the frequency of the outermost element 214a (i.e., approximately 0.5 MHz). The next inner element 214c is approximately half of the dimensions of the next outermost element 214b, resulting in a frequency of approximately 1 MHz. The innermost element 214d a cylinder or a planar disk with dimensions such that its frequency is approximately 2 MHz. Optionally, there could be an additional membrane receiver in front to the whole assembly with wideband receiving capability. For all of the elements 214, their diameter is small enough such that they produce an adequate transmit/receive beam pattern to cover the area to be imaged.

The transducer array 202 can be configured such that the receiver elements are sparsely distributed in a pseudo-random configuration over a whole hemisphere to optimize the imaging resolution. In an example of such a configuration, the transmit elements can be selected as a subset of all of the elements in the array 202. For instance, the array may contain 1372 transducer elements, of which only 128 are transmit elements. The center frequency of the transmit array can be selected to be sufficiently low so as to undergo minimal distortion and attenuation through the skull bone. As an example, the center frequency can be selected as 300 kHz.

The transducer array 202 may be operated to generate ultrasound bursts that are five or more cycles in length, with these bursts being repeated at a rate of 10 Hz or higher.

Additional operational considerations are described below. Phase correction, if ultrasound is propagated through an aberrating medium such as the skull, can be performed as described in U.S. Patent Application Ser. No. 61/771,992, which is herein incorporated by reference in its entirety.

Recording of the signals from the microbubbles throughout the imaging volume can be performed as described in U.S. Patent Application Ser. No. 61/771,992, which is herein incorporated by reference in its entirety.

The focal spot size of the hemispherical array depends on the operating frequency, and the half maximum beam width is approximately half of the wavelength. The same parameter for the length dimension is one wavelength. These dimensions are approximately 0.75 and 1.5 mm, respectively for a 1 MHz array. These dimensions can be made smaller to further increase the resolution, as described below.

First, there is evidence that at least some microbubbles show a threshold behavior as a function of the transmit pressure amplitude for the generation of second and half harmonic frequencies. This behavior can be exploited for imaging by utilizing multiple sequential transmissions at different pressure levels. For example, the pressure amplitude can be increased gradually until the desired harmonic or sub-harmonic signal is detected. This approach means that only the microbubbles at the highest pressure amplitude location are transmitting the signal and thus the source size is smaller than the actual focus. In this instance, the detected signal intensity can be assigned to a smaller image voxel, analogous to optical imaging, by repeating the sonication at a grid spacing corresponding not to the focal spot size but to the smaller volume that is above the bubble emission threshold.

In another approach, two different frequencies for the transmission sonications can be focused to the same location. Due to the microbubble nonlinearity, the microbubbles will scatter each of the transmit frequencies, as well as their difference and sum frequencies. This again is dependent on the nonlinearity of the microbubble, and thus similar methods as above could be exploited to increase the image resolution.

In another approach, multiple transmit frequencies can be used to make the transmit focus sharper.

In another approach, the phase of the transmit elements could be varied such that it rotates along the center axis of the array by 360 degrees. Thus, the elements on the opposite side of the center line would have phases that are 180 degrees out of phase. This results in a transmit beam that does not have any pressure wave travelling along the center axis, but has a circular wave with rotating phase propagating around the center axis. This configuration will result in bubble emissions from a cylindrical focal zone with a rotating phase. The locations of the echoes can then be located based on their phase.

With the systems and methods of the present invention, the imaging capabilities of clinical CT and MRI to image structures less than 300 μm in diameter can be surpassed. Because the detected microbubbles are on the order of 1-3 μm in diameter, it is contemplated that images with resolution sufficient to depict vasculature at the capillary level can be achieved with proper optimization of the transmit and receive arrays and frequencies.

The systems and methods of the present invention are unique in their ability to produce high resolution images transcranially and at depth, making them highly relevant to clinical brain imaging. The processing described above can be performed off-line, or in real-time or near real-time with the appropriate hardware.

In general, the systems of the present invention would be low cost and capable of complete vascular imaging in the brain, which would be highly advantageous to diagnostic and functional brain imaging, as well as to gaining a better understanding of brain disorders.

The systems and methods of the present invention are capable of resolutions that are superior other deep contrast ultrasound imaging techniques, and thus can also enhance ultrasound imaging in other parts of the body with suitable array geometry and operation frequency modifications for the given anatomical site.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for ultrasound imaging with an ultrasound system, the steps of the method comprising:
   a) transmitting ultrasound to a focal region in a volume-of-interest that contains at least one microbubble, using the ultrasound system;
   b) acquiring signal data in response to the transmitted ultrasound, using the ultrasound system;
   c) reconstructing a plurality of initial images by beamforming the acquired signal data;
   d) estimating a position of the at least one microbubble in each of the initial images;
   e) computing phase and amplitude correction factors using the positions estimated in step d) and the initial images reconstructed in step c);
   f) reconstructing a plurality of target images by beamforming the acquired signal data using the phase and amplitude correction factors computed in step e); and
   g) producing an image of the volume-of-interest by combining the target images, the image of the volume-of-interest having a higher spatial resolution than the target images.

2. The method as recited in claim 1 in which step g) includes combining the target images using a maximum pixel projection technique.

3. The method as recited in claim 2 in which the target images are normalized before being combined.

4. The method as recited in claim 2 in which a three-dimensional function is fit to the target images to increase the spatial resolution of the target images before they are combined.

5. The method as recited in claim 4 in which the three-dimensional function is a three-dimensional Gaussian.

6. The method as recited in claim 4 in which the three-dimensional function is a three-dimensional point spread function of an array of receive transducer elements that forms a part of the ultrasound system.

7. The method as recited in claim 2 in which step g) includes increasing the spatial resolution of the image of the volume-of-interest using a time-varying nature of the signal data acquired in step b).

8. The method as recited in claim 2 in which step a) includes tuning a transmit pressure to excite a volume that is smaller than a full width at half maximum (FWHM) of the focal region.

9. The method as recited in claim 2 in which step a) includes using an array of transducer elements to transmit the ultrasound, and in which a phase of the transducer elements is rotated along a central axis of the array.

10. The method as recited in claim 2 in which step a) includes transmitting ultrasound using a plurality of different transmit frequencies.

11. The method as recited in claim 2 in which step b) includes acquiring the signal data using multiple different receive frequencies.

* * * * *